United States Patent
Yerokhin

(10) Patent No.: US 8,852,418 B2
(45) Date of Patent: Oct. 7, 2014

(54) METHOD OF FORMING A BIOACTIVE COATING

(75) Inventor: Aleksey Yerokhin, Sheffield (GB)

(73) Assignee: Plasma Coatings Limited, North Derbyshire (GB)

( * ) Notice: Subject to any disclaimer, the term of this patent is extended or adjusted under 35 U.S.C. 154(b) by 569 days.

(21) Appl. No.: 12/739,487

(22) PCT Filed: Oct. 10, 2008

(86) PCT No.: PCT/GB2008/003432
§ 371 (c)(1), (2), (4) Date: Jul. 23, 2010

(87) PCT Pub. No.: WO2009/053670
PCT Pub. Date: Apr. 30, 2009

(65) Prior Publication Data
US 2011/0218643 A1    Sep. 8, 2011

(30) Foreign Application Priority Data
Oct. 25, 2007    (GB) .................................... 0720982.8

(51) Int. Cl.
| | |
|---|---|
| *C25D 11/00* | (2006.01) |
| *A61L 27/56* | (2006.01) |
| *C25D 11/26* | (2006.01) |
| *C25D 11/02* | (2006.01) |
| *A61L 27/32* | (2006.01) |
| *A61L 27/06* | (2006.01) |

(52) U.S. Cl.
CPC ................. *C25D 11/26* (2013.01); *A61L 27/56* (2013.01); *C25D 11/024* (2013.01); *A61L 27/32* (2013.01); *A61L 27/06* (2013.01)
USPC ............................ 205/107; 112/316; 112/317

(58) Field of Classification Search
USPC ........................................................ 205/107
See application file for complete search history.

(56) References Cited

U.S. PATENT DOCUMENTS 5,478,237 A * 12/1995 Ishizawa .................... 433/201.1
5,723,038 A *  3/1998 Scharnweber et al. ....... 205/107
(Continued)

FOREIGN PATENT DOCUMENTS

DE    10006992 A1    9/2001
EP     1818428 A1    8/2007
(Continued)

OTHER PUBLICATIONS

Yerokhin et al., "Characterisation of Oxide Films Produced by Plasma Electrolytic Oxidation of a Ti-6Al-4V Alloy" Surf. Coat. Technol. 130, pp. 195-206 (2000).*

(Continued)

*Primary Examiner* — Bryan D. Ripa
(74) *Attorney, Agent, or Firm* — Licata & Tyrrell P.C.

(57) ABSTRACT

A method for the plasma electrolytic oxidation of a bioactive coating onto implant (4) is provided. The implant is placed in an electrolyte solution (3) providing Ca and P ions and then connected to a power supply (1). A counter electrode is also provided in the electrolyte solution. A sequence of voltage pulses having alternating polarity are then applied across the implant and counter electrode to deposit a bioactive coating onto the implant. A intra-bone implant formed by the method is also provided having a coating with a thickness of 10 to 30 microns, a porosity comprised by pores with sizes of 0.5 to 10 microns, and comprising 10 to 30 wt % of hydroxyapatites.

10 Claims, 6 Drawing Sheets

(56) References Cited

U.S. PATENT DOCUMENTS

| | | | |
|---|---|---|---|
| 6,365,028 B1* | 4/2002 | Shatrov | 205/102 |
| 6,808,613 B2* | 10/2004 | Beauvir | 205/106 |
| 6,896,785 B2* | 5/2005 | Shatrov et al. | 205/109 |
| 7,166,206 B2* | 1/2007 | Chen | 205/316 |
| 2005/0221259 A1* | 10/2005 | Anderson | 433/201.1 |
| 2006/0091020 A1* | 5/2006 | Hossick-Schott et al. | 205/333 |

FOREIGN PATENT DOCUMENTS

| | | |
|---|---|---|
| RU | 2363775 C1 | 8/2009 |
| WO | WO03083181 A2 | 10/2003 |
| WO | WO2006004297 A1 | 1/2006 |

OTHER PUBLICATIONS

Yerokhin et al., "Oxide Ceramic Coatings on Aluminum Alloys Produced by a Pulsed Bipolar Plasma Electrolytic Oxidation Process" Surf. Coat. Technol. 199, pp. 150-157 (2005).*

Ni et al., "Preparation of Hydroxyapatite-containing Titania Coating on Titanium Substrate by Micro-Arc Oxidation" Mater. Res. Bull. 43, pp. 45-53 (2008).*

Heaney et al., "Absorbability of Calcium Sources: The Limited Role of Solubility" Calcif. Tissue Int. 46, pp. 300-304 (1990).*

Chen et al. "Preparation and Properties of Hydroxyapatite-containing Titania Coating by Micro-arc Oxidation" Materials Letters 2006 60:2538-2543.

Huang et al. "Hydroxyapatite Coatings Produced on Commercially Pure Titanium by Micro-arc Oxidation" Biomedical Materials 2007 2:196-201.

Yerokhin et al. "Oxide Ceramic Coatings on Aluminum Alloys Produced by a Pulsed Bipolar Plasma Electrolytic Oxidation Process" Surface & Coatings Technology 2005 199:150-157.

* cited by examiner

TABLE 1

| Phase constituent | Concentration range (wt %) |
|---|---|
| Titanium dioxides | |
| Anatase | 10...30 |
| Rutile | 10...30 |
| Total: | 20...60 |
| Bioactive amorphous phase | |
| Amorphous compounds containing Ca, P and C | 10...60 |
| Total: | 10...40 |
| Crystalline Ca compounds | |
| $CaTiO_3$ | 0...10 |
| $CaCO_3$ | 0...10 |
| Total: | 0...10 |
| Bioactive crystalline phases | |
| Hydroxyapatite | 10...30 |
| Tri-calcium phosphate | 0...20 |
| Total: | 10...40 |

(a)

(b)

(c)

METHOD OF FORMING A BIOACTIVE COATING

This patent application is a U.S. National Stage Application of International Application No. PCT/GB2008/003432, filed Oct. 10, 2008, which claims the benefit of priority from Great Britain Application No. 0720982.8, filed Oct. 25, 2007, teachings of each of which are herein incorporated by reference in their entirety.

The present invention concerns a method of forming a bioactive coating and, in particular, a method of forming a surface coating on titanium and titanium alloy intrabone implants which promotes bioactivity. Such implants are used in various orthopaedic applications, for example as a hip replacement implant.

In this connection, titanium intra-bone implants (or Ti implants), formed of titanium (Ti) or titanium alloys, are widely used in current medical practice owing to their high strength-to-weight ratio, excellent corrosion resistance and high level of biocompatibility. However, due to the inherent bio-inert nature of Ti, post-operative rehabilitation can be a slow process due to low levels of bone-implant adhesion. Accordingly, a typical patient can require up to 6 months or more before the bone-implant adhesion has reached a sufficient working strength and during this period the implant is prone to failure even under low mechanical loading.

A further problem with Ti implants relates to differences in the stiffness of Ti and bone. During loading cycles, for example when a user is walking, the difference in stiffness results in micro-displacements at the bone-implant interface, which in turn leads to fretting fatigue type wear of the Ti implant. This wear results in the release of Ti debris into the patient's body which may influence the immune system and could ultimately lead to implant rejection.

The above wear problems have been previously addressed by the application of hard coatings, such as TiN, or by surface oxidation using thermal or electrochemical techniques. However, whilst these above treatments increase the hardness of the implant surface, and hence provide improved wear resistance, they do not provide any improvement in the bioactivity of the Ti. Consequently, the bone-implant adhesion problems described above still reside.

As a solution to these bone-implant adhesion problems, various methods have been proposed to enhance an implant's bioactive properties by depositing materials having a chemical composition similar to bone or having a structure promoting osteoinduction and osteointegration. Suitable bone-like materials include calcium phosphates with Ca to P ratios ranging from 1.4-2, for example apatites and, in particular, hydroxyapatites (HAs, Ca:P=1.4-1.67), and tri- and tetra-calcium phosphates (TCPs, Ca:P=1.5 and TTCP, Ca:P=2).

Previously, such coatings were applied by spraying precursor powder materials onto the implant surface. However, such spray coating methods resulted in thick (typically >50 microns) non-uniform surface layers having low adhesion between the coating and the implant. Furthermore, there are also problems with partial decomposition of bioactive elements. Moreover, the spray coating method is unsuitable for small-sized or geometrically complex components, especially those with high precision requirements, since the coating thickness will vary depending on the exposure of the implant surface to the spray. This leads to very pronounced non-uniformity and thereby hinders spray coatings from being used with modern intra-bone implants, and particularly hip implants, which often have complex geometries.

Alternative coating methods have also been proposed, for example, sol-gel techniques and electrochemical oxidation have been used. However, coatings produced by these techniques are generally very thin (less than 2 microns) and have poor mechanical properties, and these techniques require expensive organic precursors.

More recently, coating methods involving plasma electrolytic oxidation have been proposed. For example, U.S. Pat. No. 4,846,837 discloses a method of preparing a ceramic coated metal implant that involves surface roughening followed by anodic oxidation under spark discharges in an electrolyte containing complex-bound calcium phosphate and a dispersed phase, e.g. tri- and tetra-calcium phosphates. However, the low solubility of calcium phosphate salts limits the viability of the electrolyte. Furthermore, the phase dispersed in the electrolyte tends to decompose when involved in an anodic spark discharge. As a result, depletion of calcium occurs at the coating surface due to the outward migration of $Ca^{2+}$ cations in the discharge region. This leads to insufficient calcium content in the coating for high bioactivity, as reported by J P Schreckenbach, et al (J. Mat. Sci.: Mat. in Medicine 10 (1999) 453) (Ca:P=0.5) and E Matykina, et al (Trans. Inst. of Met. Finishing, 84 3 (2006) 125) (Ca:P=0.3 to 0.55).

Accordingly, the present invention seeks to provide a coating method that overcomes the above problems associated with the prior art.

According to an aspect of the present invention, there is provided a method for plasma electrolytic oxidation of a bioactive coating onto an implant, comprising: providing the implant to be coated in an electrolyte solution, said electrolyte solution for providing Ca and P ions; connecting said implant to a power supply; providing a counter electrode in said electrolyte solution; applying a sequence of voltage pulses across said implant and counter electrode, said sequence of voltage pulses having alternating polarity.

In this way, the coating formed has highly deconvoluted surface morphology with a fine porosity and uniform structure and exhibits excellent tribological and mechanical properties. Furthermore, the implant contains large amounts of calcium and phosphorus, as well as crystalline bioactive compounds, such as hydroxyapatites and Tri-calcium phosphates. The presence of high levels of Ca, P, and crystalline bioactive compounds provide enhanced bioactive properties. In addition, the fine porosity provides good osteoconductivity, without interfering with the cell attachment process, resulting in an enhanced bone-implant interface. Moreover, the uniform coating structure and resulting bone ingrowth leads to a gradual change in mechanical properties across the bone-implant interface, thereby eliminating stress concentrations and increasing the shear strength of the system.

Preferably, each voltage pulse has a duration of 0.5-20 milliseconds. Furthermore, preferably there is a pause of less than 10 microseconds between pulses, and more preferably the pause between pulses is 5 microseconds. These durations have been found to allow the incorporation of higher amounts of calcium and phosphorus into the coating and in-situ synthesis of crystalline bioactive compounds. Moreover, the relatively short pause/pulse OFF times result in duty cycles approaching unity. This increases the coating growth rate and facilitates direct synthesis of crystalline bioactive compounds.

Preferably, the amplitudes of the voltage pulses are increased gradually up to their peak amplitudes during the first 5-300 seconds of said step of applying the sequence of voltage pulses. In this way, excessive current spikes at the beginning of the process are avoided. Furthermore, the gradual increase in amplitude has been found to promote the formation of Ca-containing compounds.

Preferably, the step of applying a sequence of voltage pulses is continued for 0.5-30 minutes. In this way, the surface coating can be grown up to a thickness of 10 to 30 microns, allowing for improved osteointegration and high coating integrity.

Conveniently, said electrolyte solution is maintained within the range of 20° C.-50° C. during said step of applying a sequence of voltage pulses. In this way, an even distribution of coating thickness is achieved, without leading to excessive porosity or coarse surface morphology.

Conveniently, said implant and said counter electrode are spaced in the range of 20 mm-100 mm from one another. In this way, electrolyte overheating and short circuit breakdowns can be avoided, and power consumption is not unnecessarily increased.

Conveniently, said peak amplitudes of the positive voltage pulses do not exceed 550V. Furthermore, conveniently, said peak amplitudes of the negative voltage pulses do not exceed −100V. In this way, violent discharges at the sites of electric field concentrations are avoided, which could otherwise affect mechanical properties and adhesion by the formation of a coarse fused coating structure.

Conveniently, said electrolyte solution comprises aqueous calcium acetate and tri-sodium orthophosphate. Furthermore, conveniently, the electrolyte solution comprises 0.05-0.2 mol of calcium acetate and 0.025-0.1 mol of tri-sodium orthophosphate per litre of water. The above components and their concentrations provide an effective source and optimum ratio of calcium/phosphorous for the formation of the coating. The coating thereby produced has a high level of calcium and phosphates, without compromising the surface structure or the formation of insoluble sediments in the electrolyte.

Conveniently, said implant comprises titanium or a titanium alloy. In this way, the presence of the titanium in the coating process results in the formation of anatase and rutile titanium dioxides, constituting about 10-30 wt % each of the coating, and having a crystalline size of 30-50 nm. The presence of nanocrystalline anatase enhances the attachment of osteoblast cells, thereby providing basic bioactivity of the oxidised surface. The presence of hard nanocrystalline rutile contributes to the enhancement of the mechanical and tribological properties of the coating. Moreover, the bioactive phases are embedded within a titania matrix of the coating, rather than being precipitated on the surface, thereby providing the coating with better integrity and adhesion to the implant substrate.

According to a further aspect of the present invention, there is provided an intra-bone implant comprising a substrate and a coating, said coating characterised by a thickness of 10-30 microns, a porosity comprised by pores with sizes of 0.5-10 microns, and comprising 10-30 wt % of hydroxyapatites. In this way, an intra-bone implant is provided with a highly bioactive coating which promotes bone ingrowth, leading to improved bone-implant adhesion and shortened patient recovery times. Furthermore, the thickness, the fine porosity and the presence of hard rutile phase in the matrix offer excellent tribological and mechanical properties, reducing the prevalence of implant fretting fatigue.

In this way, the coating provides a highly bioactive surface encouraging bone in-growth and enhanced interface strength, and thereby shortened patient recovery times. Furthermore, the porosity and coating thickness and uniformity provides an enhanced bone-implant interface, reducing the prevalence of fretting fatigue and wear.

Conveniently, said coating further comprises 1-20 wt % of Tri-calcium phosphate. In this way, a further bioactive crystalline phase is provided to further enhance bioactivity and promote bone ingrowth.

Conveniently, the Ca/P ratio is between 1.0-3.0. These high concentrations of calcium and phosphorus within the coating provide a high level of bioactivity.

Conveniently, said substrate is titanium or a titanium alloy. Titanium offers a high strength-to-weight ratio, excellent corrosion resistance and high level of biocompatibility. Furthermore, the presence of the titanium during the coating formation stages results in the formation of anatase and rutile titanium dioxides in the coating. Anatase enhances the attachment of osteoblast cells and rutile increases the hardness of the coating to improve mechanical and tribological properties. Moreover, the bioactive phases of the coating are embedded in the titania matrix, rather than precipitated on the surface, thus providing the coating with better integrity.

Conveniently, said coating comprises rutile and anatase phases of titanium dioxide each at 10 wt % -30 wt %.

Conveniently, said rutile and anatase phases are in the ratio range of 1/3-3/1.

Conveniently, said rutile and anatase phases have a crystallite size of 30 nm-50 nm. The nanocrystalline structure has been found particularly effective at improving bioactivity and hardness.

According to a further aspect of the invention, there is provided an aqueous electrolyte solution for use in the formation of a bioactive coating, said solution comprising 0.05-0.2 mol of calcium acetate and 0.025-0.1 mol of tri-sodium orthophosphate per litre of water. This combination provides a reliable and cost effective source of the calcium and phosphorus ions. In addition the electrolyte has a good storage and in-service life, a wide window of operation temperatures, and does not generally form harsh corrosive media.

Examples of embodiments of the present invention will now be described below in detail with reference to the accompanying drawings in which.

Figures 6A, 6B:
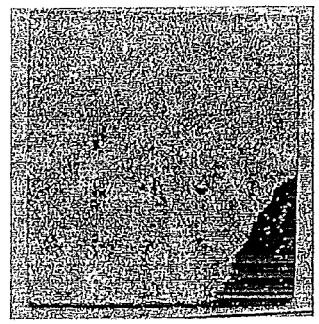
Figure 7:
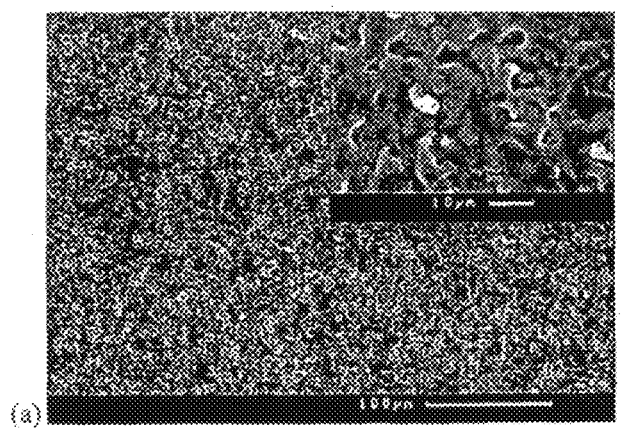
Figure 7:
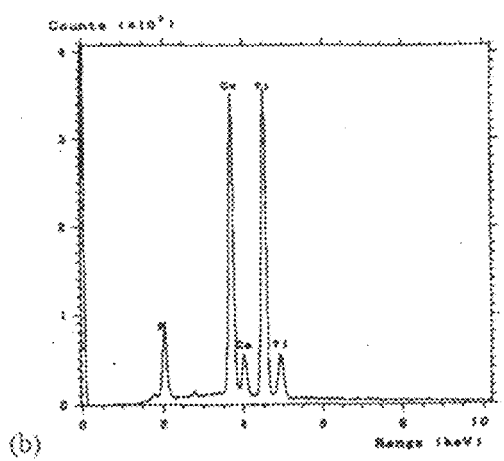
Figure 7:
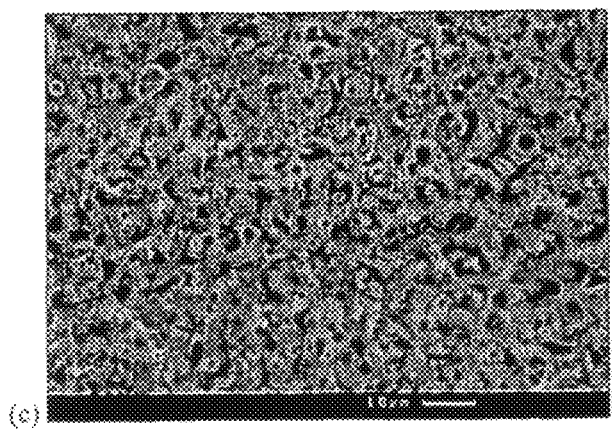
Figure 8:
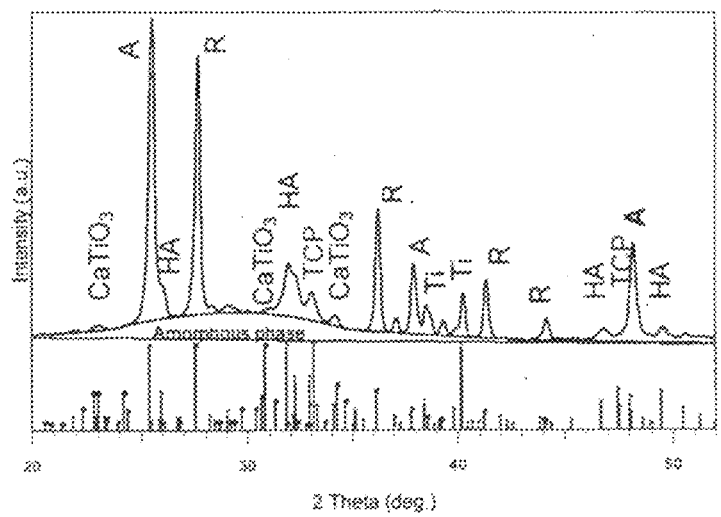
Figure 9:
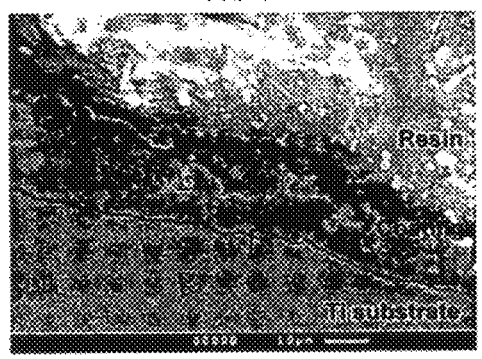
Figure 10:
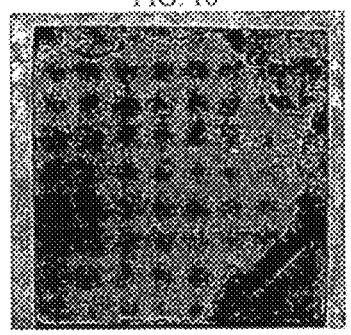

FIG. 6A shows the appearance of the coating produced under the conditions corresponding to specific example 1. The sample size is 20 mm by 20 mm. FIG. 6B shows Table 1 showing the typical phase compositions of the coatings produced by a method according to an embodiment of the present invention;

FIG. 7 shows the coating produced under conditions corresponding to specific example 1 under (a) SEM analysis of Ti surface showing details of the coating morphology revealed in the secondary electrons image mode (b) chemical composition of the surface layer obtained by EDX (carbon and oxygen are not detectable with the analyser used) and (c) Z-sensitive surface topography (backscattered electrons image mode);

FIG. 8 shows an XRD pattern of the coating on Ti produced under the conditions corresponding to specific example 1, showing characteristic peaks corresponding to calcium titanate (CaTiO3), rutile (R), anatase (A), hydroxyapatite (HA) and tri-calcium phosphate (TCP). The convex background region between 20° and 40° 2θ indicates a presence of Ca-, P- and C-containing amorphous phase;

FIG. 9 shows an SEM micrograph representing typical cross-sectional structure of the surface layer produced under conditions corresponding to specific example 2;

FIG. 10 shows the typical appearance of the coating produced under the conditions corresponding to specific example 3. The sample size is 20 mm by 20 mm; and A method according to a embodiment of the present invention will now be described in reference to the accompanying figures.

Firstly the electrolyte solution is prepared. 0.05-0.2 mol of calcium acetate and 0.025-0.1 mol of tri-sodium orthophosphate is dissolved per litre of purified water. These components provide the source of Ca and P ions for incorporation into the surface layer. Moreover, this electrolyte solution has a good storage and in-service live, and a wide window of operational temperatures. Furthermore, since the electrolyte pH and conductivity lie within the ranges 5-10 and 7-15 mS cm$^{-1}$, respectively, the required current densities can be achieved without the formation of harsh corrosive media.

The implant 4 to be coated is formed of Ti or Ti alloy. The implant 4 is immersed into tank 2 containing the electrolyte solution 3 formulated in accordance with the above. A cover is provided over sections of the implant 4 which are not to be coated.

The tank 2 is provided with a heat exchanger 6, through which the electrolyte solution 3 is circulated. During the coating process, the heat exchanger maintains the electrolyte solution 3 at a working temperature of 20° C. to 50° C.

A counter electrode 5 is provided in the tank 2 in the electrolyte solution 3. The electrode 5 is spaced in the range of 20 mm to 100 mm from the implant and is kept as uniformly spaced from the implant 4 as possible. In order to achieve uniform spacing, particularly with complex implant shapes, auxiliary electrodes may be provided.

The implant 4 and counter electrode 5 are connected to a power supply 1 and form the electrodes for the oxidation process.

Figure 1:
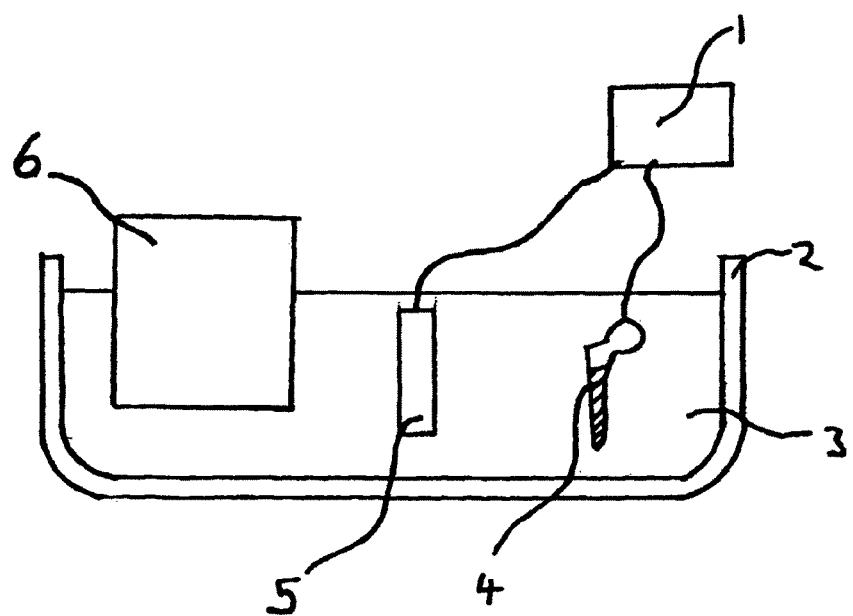
FIG. 1 is schematic diagram showing the electrolyte tank for use in the method of the first embodiment of the present invention.
Figure 2:
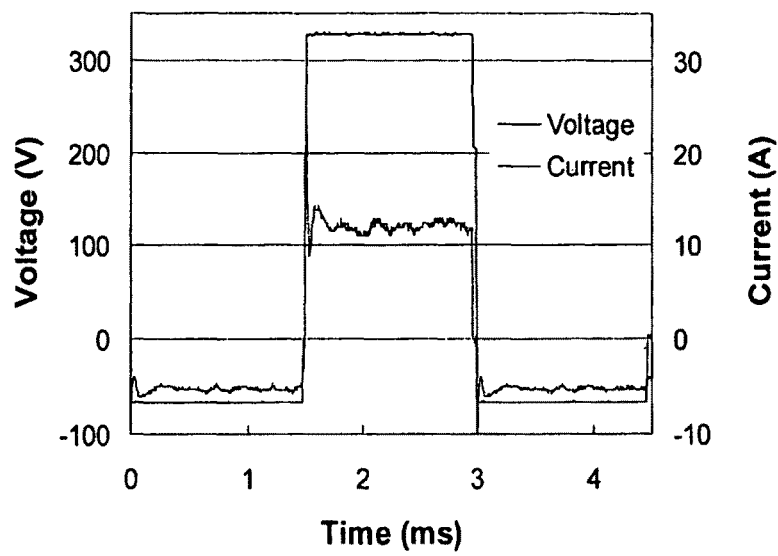
FIG. 2 shows a schematic diagram of an example voltage waveform used in the first embodiment of the present invention.

The current mode applied during the oxidation process is represented by a sequence of voltage pulses of alternating polarity. FIG. 2 shows a schematic diagram of an example voltage waveform as used in the first embodiment of the present invention. Durations of the pulses are selected within the range of 0.5 to 20 milliseconds, whereas the pauses between pulses are set at about 5 microseconds.

Figure 3:
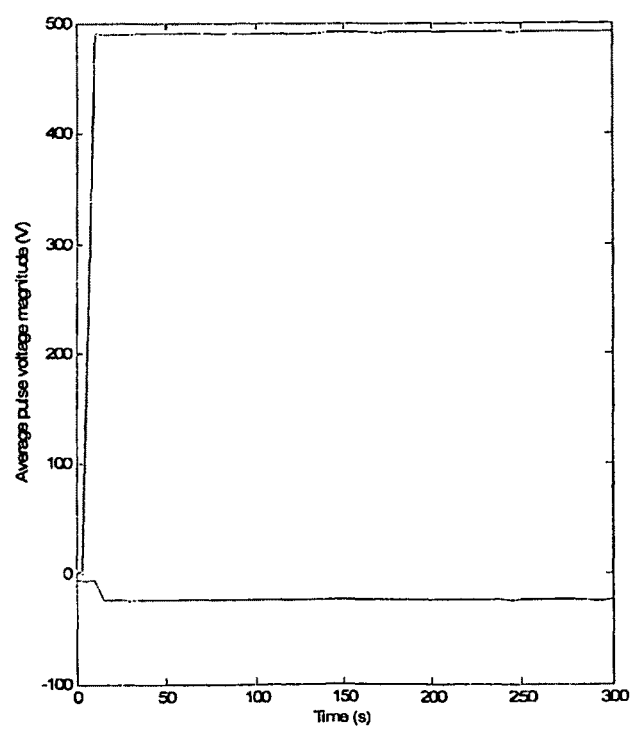
FIG. 3 shows the pulse voltage amplitude loading pattern used in the first embodiment of the present invention.

Control of the pulse amplitudes is achieved accordance with the loading pattern shown in FIG. 3. During the initial period of 5 to 300 seconds of the treatment, the amplitudes of positive and negative voltage pulses are gradually increased from 0 to a peak positive value of 300V to 550V and 0 to a peak negative value of −20V to −100V, respectively. Following this, the voltage pulses are maintained at their peak amplitudes for 0.5 to 30 minutes. This 2-step control over the amplitude of voltage pulses allows the avoidance of an excessive current spike at the beginning of the process. Furthermore, this loading pattern helps in adjusting the ratio of titanium oxides to Ca-containing compounds in the surface layer.

It should be noted that the positive voltage should not exceed 500 to 550V and the negative voltage should not exceed −100V, as this triggers powerful violent discharges at the places of electric field concentration. This would lead to the formation of a coarse fused coating structure with reduced mechanical properties and adhesion.

Figure 4:
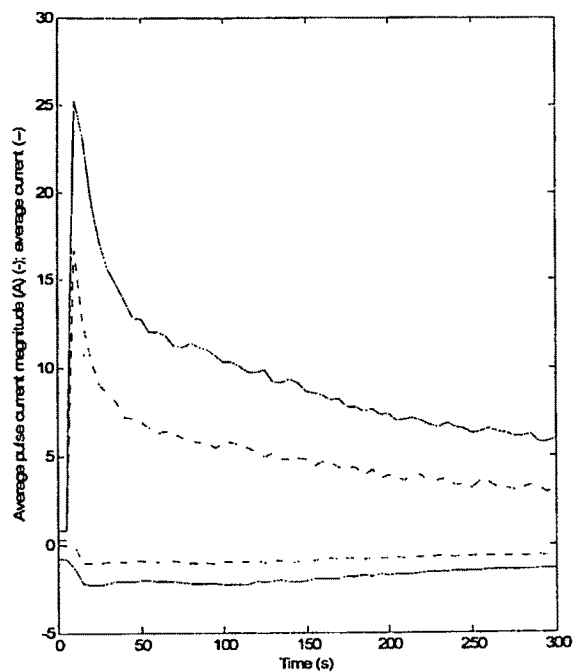
FIG. 4 shows the change in the average pulse current amplitudes during the voltage loading pattern shown in FIG. 3.

In accordance with the voltage loading pattern described above, the average pulse current densities increase initially to reach the maximum values, ranging from 0.5 to 5 A cm$^{-2}$ and from 0.05 to 0.5 A cm$^{-2}$ for positive and negative pulses, respectively. After that, the current densities decrease progressively, reflecting the coating growth process, to approach eventually the minimum values, ranging respectively from 0.01 to 1 A cm$^{-2}$ and from 0.05 to 0.5 A cm$^{-2}$. FIG. 4 shows the change in the average current pulse amplitudes during this period.

After the treatment is completed, the implant is taken out of the tank, rinsed with water and dried.

The coating produced on the implant by the above method has been found to have the following characteristics:
  a hard, well-adherent and uniform structure, with a diverse and fine porosity;
  10 to 30 micron thickness, even on components of complex 3D geometry;
  high concentrations of Ca and P sufficient to provide high bioactivity; and
  direct synthesis and incorporation into the surface structure of crystalline bioactive phases.

Figure 5:
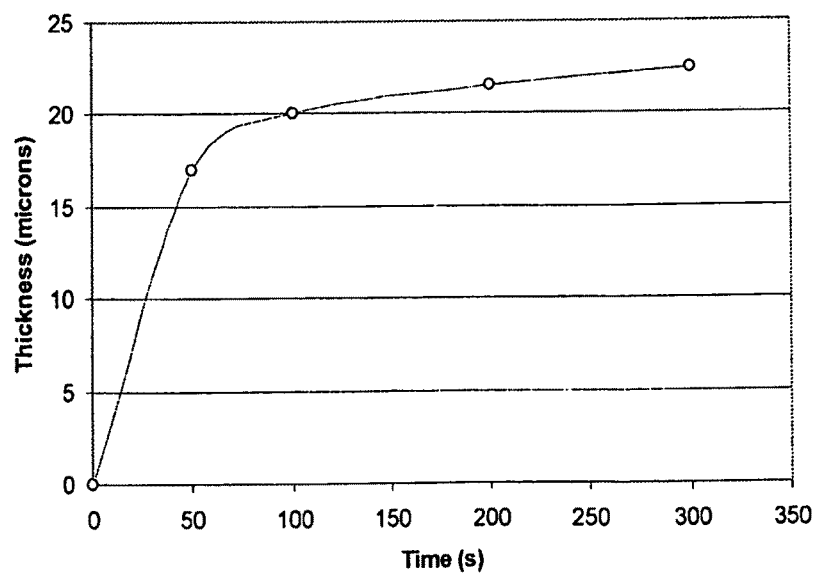
FIG. 5 shows the thickness of the coating can be varied depending on the length of the treatment time applied.

With regard to the coating thickness, it has been found that this can be controlled, as required, depending on the length of the treatment, time applied. In this connection, FIG. 5 shows how the thickness of the coating can be varied depending on the length of the treatment time applied.

The coating surface itself features a highly deconvoluted morphology, with diverse porosity formed by pores, ranging from about 0.05 to 10 microns, and minimal or no cracks.

EDX analysis of the coating shows the presence of some Ti along with significant amounts of Ca and P, with the Ca:P ratio between 1.0 to 3.0. Furthermore, Z-sensitive SEM analysis (back scattered electrons mode) shows uniform distribution of the above elements across the surface.

XRD analysis of the phase composition of the coatings produced by the above process shows the presence of both crystalline and amorphous phases. Quantitative estimations indicate that the coatings are formed by three main structural constituents, i.e. titanium dioxides (20 to 60%) bioactive amorphous phases (10 to 40%) and bioactive crystalline phases (10 to 40%). Minor (up to 10%) additions of crystalline Ca-containing phases can also be observed. Table 1 shows the typical phase compositions of the coatings produced by the above method.

It is understood that the above method enables the formation of the bioactive coating because the alternating current pulses combines both anodic and cathodic treatments in one process, thereby facilitating the incorporation of both calcium and phosphorus into the coating. In particular, the application of current pulses with reversed/negative polarity boosts Ca content in the electrolyte adjacent to the implant, which is acting as an electrode. During the subsequent positive voltage pulse, micro-discharges are generated at the implant-electrolyte interface, causing plasma assisted thermal-chemical interactions of Ca$^{2+}$ ions with components of both the electrolyte and the implant substrate.

The duration of the voltage pulses results in high amounts of calcium and phosphorus into the coating, as well as the formation of crystalline bioactive compounds, and in particular hydroxyapatite (HA) and Tri-calcium phosphate (TCP). Moreover, the relatively short pulse OFF times results in duty cycles approaching unity. This increases the coating growth rate and, importantly, facilitates direct synthesis of crystalline bioactive compounds (e.g. HA and TCP) within plasma micro-discharge regions during plasma electrolytic oxidation (PEO). This provides a unique plasma assisted route for in-situ formation of crystalline bioactive compounds on the surface which results improved coating morphology and a more uniform thickness.

Compared to other HA-containing coatings directly synthesised by plasma electrolytic oxidation (PEO), the coatings produced by the above method have better uniformity, mechanical properties and adhesion. Also they show better bioactivity compared to PEO films produced using conventional techniques. Furthermore, they do not contain potentially hazardous elements, such as Cl. The highly deconvoluted, porous and virtually crack-free surface morphology provides an excellent interface between the metal implant and the bone since the mechanical properties are gradually transformed from the bone to the implant substrate, minimising any stress concentrations, and thereby increasing substantially the system's shear strength. Moreover, the fine porosity provides good osteoconductivity, without interfering with the cell attachment process.

The coating's substantially improved bioactive properties are provided by the presence Ca and P, in high concentrations and in appropriate proportions. These bioactive phases are embedded into a titania matrix, rather than precipitated on the surface, thus providing surface a layer with better integrity and adhesion.

Furthermore, as demonstrated by the various analysis methods discussed above, a variety of crystalline and amorphous phases containing Ca and P are present. These phases have different pH stability ranges and solubility constants and, in terms of solubility, can be ranked in the following ascending order:

$CaTiO_3 < HA < TCP < $ Amorphous Ca, P compounds $< CaCO_3$

This composition ensures gradual release (through the porosity channels) of Ca and P ions to contribute to the proliferation of osteoblast cells at the implant surface. As such a long-term bioactive effect is achieved at the surface. Moreover, uniform osteoinduction is ensured by an even distribution of Ca and P all over the coated surface.

Specific examples of the present invention will now be described.

SPECIFIC EXAMPLE 1

A sample made of commercially pure Ti with surface area of about 3.4 $cm^2$ is immersed into a stainless steel tank containing a solution of 0.1 mol of calcium acetate and 0.05 mol of tri-sodium orthophosphate per litre of purified water. The electrolyte temperature is maintained within 30-34° C. by an external heat exchange device. The distance between the tank and the Ti sample is kept within 40-50 mm.

The sample and the tank are connected to the alternative outputs of the pulse power supply and a sequence of voltage pulses of alternating polarity is supplied between them so that the durations of positive and negative pulse biasing of the Ti sample are 2.3 ms and 2.1 ms respectively. During the first 30 seconds of treatment, the corresponding amplitudes of voltage pulses are increased from 0 V to 478 V and to −32 V (see FIG. 3) and after that are maintained constant for 5 minutes. Corresponding patterns of current are shown in FIG. 4. After the treatment is complete, the sample is taken out of the tank, rinsed with water and dried.

The thickness of the resulting coating is 32.4±2.5 μm and the appearance is smooth and uniform, as illustrated by FIG. 6. The results of analysis of surface morphology and chemical composition of the coating are shown in FIG. 7. The coating has a uniform microstructure featured by a diverse porosity (FIG. 7a). It has a high content of Ca (Ca:P≈3) (FIG. 7b) and a uniform distribution of these elements across the surface area (FIG. 7c). The coating phase composition is illustrated by FIG. 8, indicating a presence of an amorphous bioactive phase (≈30%) and several crystalline phases. The crystalline constituent comprises titanium dioxide phases, including anatase (≈30%), rutile (≈25%), and bioactive crystalline phases, including HA (≈13%) TCP (≈9%) and $CaTiO_3$ (≈3%).

SPECIFIC EXAMPLE 2

A femoral implant component made of Ti-6Al-4V alloy is treated in a solution containing 0.2 mol of calcium acetate and 0.08 mol of tri-sodium orthophosphate per litre of purified water at 38-42° C. The inter-electrode distance is set within 70 to 100 mm. The pulse durations are set at 1.5 and 2.5 ms for positive and negative biasing, respectively. The corresponding voltages are ramped up to +380 V and −40V for 5 min and after that maintained at these levels for 20 min.

The thickness of the resulting coating is 16.8±2.1 micron and the cross-sectional coating morphology is shown in FIG. 9, indicating a relatively compact and uniform surface layer with no interfacial defects. The phase composition is represented by approximately 45% of amorphous phase, 15% of anatase, 15% of rutile, 25% of HA, and 5% of $CaCO_3$.

SPECIFIC EXAMPLE 3

A sample of cp-Ti with surface area of about 3.4 $cm^2$ is treated in a solution containing 0.1 mol of calcium acetate and 0.05 mol of tri-sodium orthophosphate at 58-62° C. The inter-electrode distance is kept within 40-50 mm. The durations of positive and negative pulses are 2.7 ms and 1.5 ms respectively. The pulse amplitudes are directly set at +555 V and −42 V, without the initial ramping stage. The resulting coating is less smooth and uniform than previous examples because of the appearance of discharges at the edges of the sample (FIG. 10). The coating thickness after 5 min of the treatment is 27.1±4.7 μm.

Although the present invention has been described based on the above illustrated embodiments, the present invention is not limited solely to these particular embodiments.

The invention claimed is:

1. A method for forming by plasma electrolytic oxidation a porous bioactive coating onto an implant, comprising:
providing the implant to be coated in an electrolyte solution, said electrolyte solution suitable for providing Ca and P ions and comprising 0.05-0.2 mol of calcium acetate and 0.025-0.1 mol of tri-sodium orthophosphate per liter of water;
connecting said implant to a power supply;
providing a counter electrode in said electrolyte solution; and
forming the bioactive coating on the implant from the Ca and P ions in the electrolyte solution by applying a sequence of voltage pulses across said implant and counter electrode, said sequence of voltage pulses having alternating polarity;
wherein each voltage pulse has a duration of 0.5-20 milliseconds.

2. The method of claim 1, wherein there is a pause of less than 10 microseconds between pulses.

3. The method of claim 2, wherein the pause between pulses is 5 microseconds.

4. The method of claim 1, wherein amplitudes of the voltage pulses are increased gradually up to peak amplitudes during the first 5-300 seconds of said step of applying the sequence of voltage pulses.

5. The method of claim 1, wherein the step of applying a sequence of voltage pulses is continued for 0.5-30 minutes.

6. The method of claim 1, wherein said electrolyte solution is maintained within the range of 20° C.-50° C. during said step of applying a sequence of voltage pulses.

7. The method of claim 1, wherein said implant and said counter electrode are spaced in the range of 20 mm-100 mm from one another.

8. The method of claim 1, wherein peak amplitudes of the positive voltage pulses do not exceed 550 V.

9. The method of claim 1, wherein peak amplitudes of the negative voltage pulses do not exceed −100 V.

10. The method of claim 1, wherein said implant comprises titanium or a titanium alloy.

* * * * *

UNITED STATES PATENT AND TRADEMARK OFFICE
CERTIFICATE OF CORRECTION

PATENT NO. : 8,852,418 B2  
APPLICATION NO. : 12/739487  
DATED : October 7, 2014  
INVENTOR(S) : Aleksey Yerokhin Page 1 of 1

It is certified that error appears in the above-identified patent and that said Letters Patent is hereby corrected as shown below:

On the Title Page,

Item (75) insert --Allen Matthews, Rotherham (GB)--

Signed and Sealed this  
Sixth Day of January, 2015

Michelle K. Lee  
*Deputy Director of the United States Patent and Trademark Office*

UNITED STATES PATENT AND TRADEMARK OFFICE
CERTIFICATE OF CORRECTION

| | | |
|---|---|---|
| PATENT NO. | : 8,852,418 B2 | Page 1 of 1 |
| APPLICATION NO. | : 12/739487 | |
| DATED | : October 7, 2014 | |
| INVENTOR(S) | : Aleksey Yerokhin | |

It is certified that error appears in the above-identified patent and that said Letters Patent is hereby corrected as shown below:

On the Title Page,

Item (75) insert --Allan Matthews, Rotherham (GB)--

This certificate supersedes the Certificate of Correction issued January 6, 2015.

Signed and Sealed this
Twenty-fourth Day of March, 2015

Michelle K. Lee
*Director of the United States Patent and Trademark Office*